United States Patent [19]

Boenisch et al.

[11] Patent Number: 5,350,674

[45] Date of Patent: Sep. 27, 1994

[54] INTRINSIC FACTOR - HORSE PEROXIDASE CONJUGATES AND A METHOD FOR INCREASING THE STABILITY THEREOF

[75] Inventors: Michael T. Boenisch, Owings Mills; Erica A. Sullivan, Sparks, both of Md.

[73] Assignee: Becton, Dickinson and Company, Franklin Lakes, N.J.

[21] Appl. No.: 941,352

[22] Filed: Sep. 4, 1992

[51] Int. Cl.$^5$ ............... G01N 33/566; C12N 9/96
[52] U.S. Cl. ............... 435/7.8; 435/188; 435/962; 435/964; 435/975
[58] Field of Search ............ 435/7.8, 188, 975, 964, 435/962

[56] References Cited

U.S. PATENT DOCUMENTS

| | | | |
|---|---|---|---|
| 5,104,815 | 4/1992 | Garner et al. | 436/505 |
| 5,118,791 | 6/1992 | Burnier et al. | 530/326 |
| 5,132,226 | 7/1992 | Dreher et al. | 436/512 |

FOREIGN PATENT DOCUMENTS 8912826A 12/1989 PCT Int'l Appl. .

OTHER PUBLICATIONS

Derksen et al., Biochimica et Biophysica Acta, vol. 814 (1985), 151–155.
Hashida et al., J. Applied Biochem., vol. 6 (1984), 56–63.
Waters et al., J. Clin. Pathol., vol. 42 (1989), 307–312.
Yoshitake, S. et al, Analytical Letters, 15(B2), Efficient Preparatoin of Fab'–horseradish peroxidase Conjugates Using Maleimide Compounds and Its Use For Enzyme Immunoassay (1982), pp. 147–160.
Teale et al, J. Mol. Cell. Immunol. 2, pp. 283–292, (1986).
Duncan et al., Anal. Biochem., 132, pp. 68–73 (1983).
Saunders, "Immunoassays in the Clinical Laboratory," Alan Liss, Inc. N.Y., N.Y. (1979) pp. 99–118.
Wilson & Nakane, "Immunofluorescence and Related Staining Techniques," G. Elsevier/North–Holland Biomedical Press, Amsterdam, (1978) pp. 215–224.
Wang, Clin. Chem., vol. 33, No. 6, Abst. 403 (1987).
Leonard, Clin. Chem., vol. 35, No. 6, Abst. 609 (1989).
Quinn, Clin. Chem., vol. 37, No. 6, Abst. 326 (1991).
Timmons, Clin. Chem., vol. 38, No. 6, Abst. 662 (1992).
Mansbach, Clin. Chem., vol. 38, No. 6, Abst. 691 (1992).

*Primary Examiner*—Mary E. Ceperley
*Attorney, Agent, or Firm*—Bruce S. Weintraub

[57] ABSTRACT

This invention presents a non-isotopic competitive assay for Vitamin B12 (B12), utilizing intrinsic factor (IF) labelled with horse radish peroxidase (HRP), by coupling via heterobifunctional cross-linking agents. In addition, a method for stabilizing the resultant conjugates by pretreatment with N-ethylmaleimide is disclosed.

7 Claims, No Drawings

INTRINSIC FACTOR - HORSE PEROXIDASE CONJUGATES AND A METHOD FOR INCREASING THE STABILITY THEREOF

BACKGROUND OF INVENTION

Assays for the serum level of Vitamin B12 have proven to be extremely challenging to develop. This is due primarily to the high sensitivity required, on the level of picograms, as well as the fact that normal serum contains endogenous B12 binders. These binders must be treated to release the B12 prior to the assay; such treatment is quite harsh and generally requires a separate step to accomplish it. Generally, the treatment involves the use of either heating to elevated temperatures (100° C.), commonly termed "boil" assays, or the use of strong chemical agents, "no-boil" assays. One example of a no boil assay is presented in U.S. Pat. No. 4,300,907 to Mansbach et al.

Because of these requirements, until quite recently virtually all commercially available assays for B12 have been radio assays which utilize a radioactive isotopic labeled binding protein for detection. A number of other formats have been discussed in the literature including the use of chemiluminescent (Clin. Chem. Vol. 35, No. 6, p.1194, Abstract No. 609, (1989)), fluorescent (Clin. Chem. Vol. 37, No. 6 , p. 978, Abstract No. 326 (1991)), and color-labelled B12 (available from Ciba Corning) detectors. These assays utilize microbeads coated with B12 binding protein for detection, and, as such, are not compatible with many automated detection methods.

Additionally, enzyme linked assays utilizing alkaline phosphatase (Clin. Chem. Vo. 38, No. 6, p. 1095, Abstract 0691 (1992) and B galactosidase (Clin. Chem. Vo. 33, No. 6, p. 963, Abstract 403 (1989)) have been reported; however, both of these enzymes are quite large. Since the time required for competitive immunoassays is heavily dependent on the diffusion rate, and since the diffusion rate is approximately inversely proportional to the cube root of the molecular weight, the utility of these formats in such assays is limited.

SUMMARY OF INVENTION

This invention presents a non-isotopic competitive assay for Vitamin B12 (B12). Briefly, the assay utilizes intrinsic factor (IF) labelled with horse radish peroxidase (HRP). The HRP can be conjugated to the IF by coupling via heterobifunctional cross-linking agents.

This method, it has been found, permits formation of the IF/HRP conjugate without deleteriously affecting the B12 binding sites on the IF. Thus the conjugates can be used in assays for B12. Further, because the IF is labelled with HRP, the assays can be run on automated equipment adapted to utilize the signal generated by the HRP/substrate reaction. Additionally because the method permits relatively large amounts of HRP to be conjugated to IF (i.e. a high HRP/IF ratio), the signal generated will also be high, increasing the assay sensitivity.

In addition, a method for stabilizing the resultant conjugates by pretreatment with N-ethylmaleimide is disclosed. This stabilization permits storage of the conjugates for extended periods of time.

DETAILED DESCRIPTION OF THE INVENTION

The assays of this invention make use of the well known binding affinity of intrinsic factor (IF) for Vitamin B12 (B12). Briefly, in a preferred competitive assay format, the (liquid) sample (which may contain B12) is mixed with IF conjugated to horse radish peroxidase (HRP) and permitted to react. An aliquot of this mixture is then placed in contact with a solid phase containing bound B12. Subsequently, the liquid phase is separated from the solid phase, leaving behind any IF/HRP bound to the solid phase B12; any IF/HRP bound to sample B12 remains in the liquid. The amount of IF/HRP conjugate in the sample can then be measured by addition of HRP substrate and measurement of the reaction product. This is directly related to the quantity of B12 in the sample. Alternatively, the activity of the bound IF/HRP conjugate would be determined to ascertain B12 in the sample indirectly.

The substrate utilized is any amenable to HRP action; preferred substrates include: tetramethyl benzidine, o-phenylenediamne, luminol/iodophenol, and tyramine.

Coupling of the HRP to the IF is a critical requirement of this assay. Since many coupling methods require treatment with chemicals which can deleteriously affect the IF and/or HRP, the treatment must be sufficiently mild to permit both of these components to remain unaffected, yet sufficiently strong to permit formation of a conjugate which will not dissociate under storage and/or assay conditions.

In one such method, the HRP can be conjugated to the IF via heterobifunctional succinimidyl-4-(p-maleimidophenyl) butyrate (SMPB) and N-succinimidyl-5-acetylthioacetate (SATA). The use and preparation of HRP conjugates using SATA are described in Duncan et al., Anal. Biochem, 132, pp. 68—73 (1983), and the use of SMPB to couple to antibodies is described in Teale et al., J. Mol. Cell Immunol., 2, PP. 283–292 (1986) and Yoshitake et al., Anal. Letters. 15, p. 147-160 (1982), all three of which are incorporated herein by reference.

Briefly, SATA is reacted with HRP and SMPB is reacted with IF in separate processes. The SATA-HRP is then reacted with the SMPB-IF to form a HRP-SATA-SMPB-IF conjugate. More specifically, HRP is dissolved in an aqueous buffer, preferably phosphate buffered saline, containing a chelating agent, preferably 1 mM EDTA. The concentration of HRP in buffer is 1–50 gm/l, preferably 5–25 gm/l, more preferably 10–15 gm/l. This solution is mixed with 150–350 mM, preferably 200–300 mM, SATA in dimethyl formamide (DMF) at a SATA-HRP (mole/mole) ratio of 3–10:1, preferably 4–6:1. The unreacted SATA is subsequently removed and the resultant SATA-HRP conjugate is deacetylated by the addition of a solution of a deacylating agent, preferably hydroxylamine hydrochloride at a rate of 10 μl of 50 mM per mg SATA-HRP.

SMPB-IF conjugate is prepared by dissolving SMPB in the same solvent as SATA, at a concentration of 5-35 mM. preferably 20-30 mM. this is reacted with 0.1-g/l, preferably 0.3–0.7 g/l IF, dissolved in the same buffer as the HRP, at a SMPB:IF ratio of 50-250:1, preferably 75-125:1. The reaction proceeds at ambient temperature, and the unreacted SMPB is subsequently removed.

The resultant SMPB-IF conjugate is reacted with the deacylated SATA-HRP conjugate by dropwise addition of the deacylated SATA-HRP to a final HRP:IF ratio of about 10–30:1, preferably 15–25:1. The product is then dialyzed against the same buffer and glycerol or suitable diluent is added to facilitate storage.

In a further modification of the above procedure, the stability of the resultant conjugates can be enhanced by pretreatment of the IF with N-ethylmaleimide. Such treatment is commonly used to block free sulfhydryl groups prior to such reactions, which would tend to form protein dimers linked by SMPB. However, since such formation is not observed to any appreciable magnitude with IF, and since IF does not have any free sulfhydryls, the stabilization conferred on the conjugates is quite surprising.

To effect pretreatment, NEM is dissolved in the same solvent as the IF to a concentration of 1–2 mg/ml, preferably 1.3–1.5 mg/ml. This is admixed with the IF solution at an NEM:IF ratio of 50:1–200:1, preferably 75:1–150:1, more preferably 100:1; the entire mixture is shielded from light and permitted to react at 25°–30° C. for 60 minutes. Immediately thereafter, the SMPB solution is added to the mixture and the SMPB-IF conjugate is formed as described above; NEM is subsequently removed by any convenient means preferably by desairing chromatography, and the conjugate is ready for use.

Either of the above conjugates can be utilized in the competitive assay for Vitamin B12 as described above. The above procedures are particularly suited for making HRP-IF conjugates as they minimize the use of expensive IF, by utilizing an excess of HRP (or SATA-HRP and SMPB) to assure all IF is reacted, in addition to leaving the HRP and IF relatively intact and functionally unaffected.

Further, the above assay procedure, using HRP-IF conjugates, is particularly suited for use in automated assay instruments, such as the AFFINITY ® analyzer manufactured and marketed by Becton, Dickinson and Company, due to the fact that HRP activity is measured. As many assays can be formatted to use HRP as the tracer or detector, the versatility of such an assay and, thus, such an instrument is enhanced.

EXAMPLES

The following examples demonstrate certain preferred embodiments of the instant invention, but are not intended to be illustrative of all embodiments.

Example 1 - Preparation of HRP-SATA-SMPB-IF

HRP was dissolved in phosphate buffered saline containing 1 mM EDTA (PBS/EDTA) at a concentration of 12 mg/ml. Concurrently N-succinylimidyl-S-acetylthio-acetate (SATA) was dissolved in dimethylformamide (DMF) to a 240 mM concentration. These solutions were subsequently mixed, at a SATA:HRP ratio (3) if 4.8:1, and incubated at 20°–25° C. for 15 minutes. Unreacted SATA was then removed by dialysis against PBS/EDTA.

The resultant SATA-HRP conjugates were then deacetylated by the addition of 10 μl of 50 mM hydroxylamine hydrochloride in PBS/EDTA (pH 7.5) per mg SATA-HRP, and allowed to react for 3 hours, at 20°–25° C., shielded from light.

Concurrently with the deacetylation, succinimidyl-4-(p-maleimidophenyl) butyrate (SMPB) was dissolved in DMF to a concentration of 22.8 mM. This was mixed with a 0.5 mg/ml solution of IF in PBS-EDTA, at a SMPB:IF ratio (mole:mole) of 100:1. This system was incubated for 30 minutes at 20°–25° C., shielded from light, after which unreacted SMPB was removed by desalting chromatography.

The resultant SMPB-IF conjugate was then admixed with the deacetylated SATA-HRP at an HRP:IF ratio (mole:mole) of 20:1, and reacted for 2 hours at 20°–25° C., shielded from light. The resultant conjugate was then dialyzed against PBS-EDTA for 24 hours at 2°–8° C. shielded from light. The resultant solutions was admixed with an equal volume of glycerol, and stored at −18 to −22° C.

Example 2 - Preparation of Stabilized HRP-SATA-SMPB-IF Conjugates

The procedure of Example 1 was repeated except that the IF was reacted with N-ethylmaleimide (NEM) prior to conjugation with SMPB. The NEM was dissolved in PBS/EDTA at a concentration of 1.43 mg/ml, and was admixed with the 0.5 mg/ml solution of IF at a molar ratio of NEM/IF of 100:1. The mixture was allowed to react at 20°–25° C., for one hour, shielded from light. After the reaction, unreacted NEM was removed by desairing chromatography, and the resultant IF was used as in Example 1.

Example 3 - Stability of Conjugates

To assess the stability of the conjugates prepared in Examples 1 and 2, quantities of each were stored by varying periods of time and tested for activity by a competitive assay wherein bound B12 in a coated tube competes with free B12 for IF-HRP. All IF-HRP reacting with the sample (free) B12 is removed from the tube and the B12 concentration is determined by monitoring HRP activity remaining in the tube.

The results are presented below:

|  | % Activity Loss | |
| Storage Time/Temp. | Example 1 | Example 2 |
| --- | --- | --- |
| Fresh | 0 | 0 |
| 15 days/4° C. | 0 | 1.06 |
| 15 days/37° C. | 30.04 | 3.98 |

As shown, the fresh conjugates gave the same results, demonstrating that the NEM has no affect on the fresh IF. This is consistent with the absence of free sulfhydryl groups in IF. However, the example 2 conjugates are far more stable upon extended and higher temperature storage, indicative of the stabilizing effect of NEM treatment.

It is apparent that many modifications and variations of this invention as hereinabove set forth may be made without departing from the spirit and scope hereof. The specific embodiments descried are given by way of example only and the invention is limited only by the terms of the appended claims.

What is claimed is:

1. A method for producing a stabilized HRP-SATA-SMPB-IF conjugate comprising:
 (i) admixing intrinsic factor (IF) with N-ethylmaleimide (NEM) to form an NEM/IF product;
 (ii) reacting said NEM/IF product with succinimidyl-4- (p-maleimidophenyl) butyrate (SMPB) to form a SMPB-IF product;
 (iii) reacting horseradish peroxidase (HRP) with N-succinylimidyl-5-acetylthioacetate (SATA) to form a SATA-HRP product, and subsequently deacetylating said product to form a deacetylated SATA-HRP product;

(iv) admixing said SMPB-IF product with said deacetylated SATA-HRP product to form a HRP-SATA-SMPB-IF conjugate; and (v) subsequently concentrating said conjugate.

2. The method of claim 1 wherein the NEM/IF product is produced by reacting NEM with IF at an NEM-/IF (mole:mole) ratio of 50–200/1.

3. The method of claim 2 wherein said SATA-HRP product is deacetylated by the addition of hydroxylamine hydrochloride.

4. The method of claim 2 wherein said HRP-SATA-SMPB-IF conjugate is prepared by reacting said deacetylated SATA-HRP product with said SMPB-IF product at a HRP/IF (mole:mole) ration of 10–30/1.

5. The method of claim 2 wherein the concentration is achieved by dialysis.

6. A stabilized HRP-SATA-SMPB-IF conjugate produced by the method of claim 1.

7. In a kit for the competitive assay of Vitamin B 12, which kit includes a horse radish peroxidase-intrinsic factor conjugate as a tracer, the improvement which comprises providing, as said tracer, the HRP-SATA-SMPB-IF conjugate of claim 6.

* * * * *